United States Patent [19]
Hopkins

[11] Patent Number: 5,948,489
[45] Date of Patent: *Sep. 7, 1999

[54] CATHETER HAVING EXTRUDED, FLEXIBLE, PLIABLE AND COMPLIANT MARKER BAND

[75] Inventor: Ronald J. Hopkins, Pembroke Pines, Fla.

[73] Assignee: Cordis Corporation, Miami Lakes, Fla.

[*] Notice: This patent issued on a continued prosecution application filed under 37 CFR 1.53(d), and is subject to the twenty year patent term provisions of 35 U.S.C. 154(a)(2).

[21] Appl. No.: 08/734,122

[22] Filed: Oct. 21, 1996

Related U.S. Application Data

[63] Continuation of application No. 08/205,616, Mar. 3, 1994, abandoned.

[51] Int. Cl.[6] .............................. B32B 1/08; B32B 27/20; B32B 27/32; B32B 27/40
[52] U.S. Cl. ...................... 428/34.9; 428/36.9; 428/328; 428/343; 428/423.1; 428/500; 428/523; 604/96; 604/264; 604/280
[58] Field of Search ................................ 428/34.9, 35.1, 428/36.9, 323, 328, 343, 423.1, 500, 523; 128/772, 657, 658; 604/96, 280, 282, 284, 283, 264

[56] References Cited

U.S. PATENT DOCUMENTS

| | | | |
|---|---|---|---|
| 4,195,637 | 4/1980 | Gruntzrg | 604/280 |
| 4,292,970 | 10/1981 | Hession, Jr. | 604/164 X |
| 4,323,071 | 4/1982 | Simpson et al. | 604/280 |
| 4,420,083 | 12/1983 | Ganz et al. | 604/283 |
| 4,516,970 | 5/1985 | Kaufman et al. | 604/270 |
| 4,545,390 | 10/1985 | Leary | 604/280 |
| 4,661,094 | 4/1987 | Simpson | 604/53 |
| 4,681,110 | 7/1987 | Wiktor | 128/343 |
| 4,863,442 | 9/1989 | De Mello et al. | 604/282 |
| 4,920,980 | 5/1990 | Jackowski | 128/786 |
| 4,967,753 | 11/1990 | Haase et al. | 128/662.06 |
| 5,045,071 | 9/1991 | McCormick et al. | 604/280 |
| 5,084,022 | 1/1992 | Claude | 604/164 |
| 5,088,927 | 2/1992 | Lee | 433/224 |
| 5,114,401 | 5/1992 | Stuart et al. | 604/53 |
| 5,116,652 | 5/1992 | Alzner | 428/36.9 |
| 5,221,270 | 6/1993 | Parker | 604/282 |
| 5,253,653 | 10/1993 | Daigle et al. | 128/772 |
| 5,256,158 | 10/1993 | Tolkoff et al. | 604/280 |
| 5,267,574 | 12/1993 | Viera et al. | 128/772 |
| 5,343,543 | 8/1994 | Novak, Jr. et al. | 385/31 |
| 5,364,352 | 11/1994 | Cimino et al. | 604/95 |
| 5,368,048 | 11/1994 | Stoy et al. | 128/772 |
| 5,413,557 | 5/1995 | Solar | 604/96 |
| 5,465,733 | 11/1995 | Hinohara et al. | 128/772 |

OTHER PUBLICATIONS

Encyclopedia of Polymer Science and Engineering, vol. 1 p. 522, vol. 7 p. 81, ©1987 J. Wiley & Sons.

Primary Examiner—Vivian Chen
Attorney, Agent, or Firm—Michael W. Montgomery

[57] ABSTRACT

A tubular catheter body comprising a catheter consisting essentially of plastic material and having a tubular, flexible, and compliant marker band affixed to and surrounding the external surface of the catheter body. The compliant marker band comprises a heat shrinkable plastic material having tungsten particles which are no greater than 2 microns in size such that the marker band is radiopaque throughout.

10 Claims, 1 Drawing Sheet

CATHETER HAVING EXTRUDED, FLEXIBLE, PLIABLE AND COMPLIANT MARKER BAND

This application is a continuation of application Ser. No. 08/205,616, filed Mar. 3, 1994, abandoned.

BACKGROUND OF THE INVENTION

1. Field of the Invention

The present invention relates to a complaint radiopaque marker band which comprises a flexible plastic carrier material having mixed therein minute particles of metal. One preferred metal is tungsten having a particle size of 0.9 microns.

2. Description of the Related Art Including Information Disclosed Under 37 CFR §§ 1.97–1.99.

Heretofore, various types of marker bands have been proposed for placement on a guidewire or on a catheter. Several examples of such marker bands positioned on or in a guidewire or catheter are disclosed in the following U.S. Patents:

| U.S. Pat. No. | Patentee |
| --- | --- |
| 4,681,110 | Witkor |
| 4,516,970 | Kaufman et al. |
| 5,084,022 | Claude |
| 5,114,401 | Stuart, et al. |
| 5,116,652 | Alzner |
| 5,253,653 | Daigle, et al. |
| 5,267,574 | Viera, et al. |

The non-analolgous Kaufman et al. U.S. Pat. No. 4,516,970 discloses a feeding tube element having a bolus tip element composed of a mixture of powdered metal such as tungsten, copper, tantalium or brass and a synthetic plastic binder for same, such as polyurethane, silicone, polyvinylchloride or polyphosphazane. The weighted bolus tip facilitates insertion of the feeding tube to the stomach and the tip element being made of plastic binder and metal powder eliminates the problem of metal spillage.

The Witkor U.S. Pat. No. 4,681,110 discloses a catheter arrangement having a blood vessel liner and includes metal staples that can be carried by the liner to serve as x-ray markers.

The non-analogous Alzner U.S. Pat. No. 4,116,652 discloses a kink resistant tubing or catheter comprising a metal ionomer, polyamide and polyurethane.

The Claude U.S. Pat. No. 5,084,022 discloses a guidewire having narrow bands or marks formed by electro-chemical etching of a metal wire forming at least part of the guidewire.

The Stuart, et al. U.S. Pat. No. 5,114,401 discloses a catheter having markings thereon.

The Daigle, et al. U.S. Pat. No. 5,253,653 discloses a guidewire having mounted on a core wire thereof a linear array of radiopaque markers.

The Viera, et al. U.S. Pat. No. 5,267,574 discloses a guidewire having highly radiopaque marker bands spaced from each other along a segment of a core wire of a guidewire to aid a physician in monitoring the position of the guidewire.

SUMMARY OF THE INVENTION

According to the present invention there is provided a compliant marker band material made of a plastic material having metal particles thoroughly mixed therein such that when the plastic material with the particles therein is extruded, the extruded tube is highly radiopaque and can be cut to desired lengths for use as marker bands on or in a catheter or a guidewire sheath.

DESCRIPTION OF THE PREFERRED EMBODIMENT(S)

Figure 1:
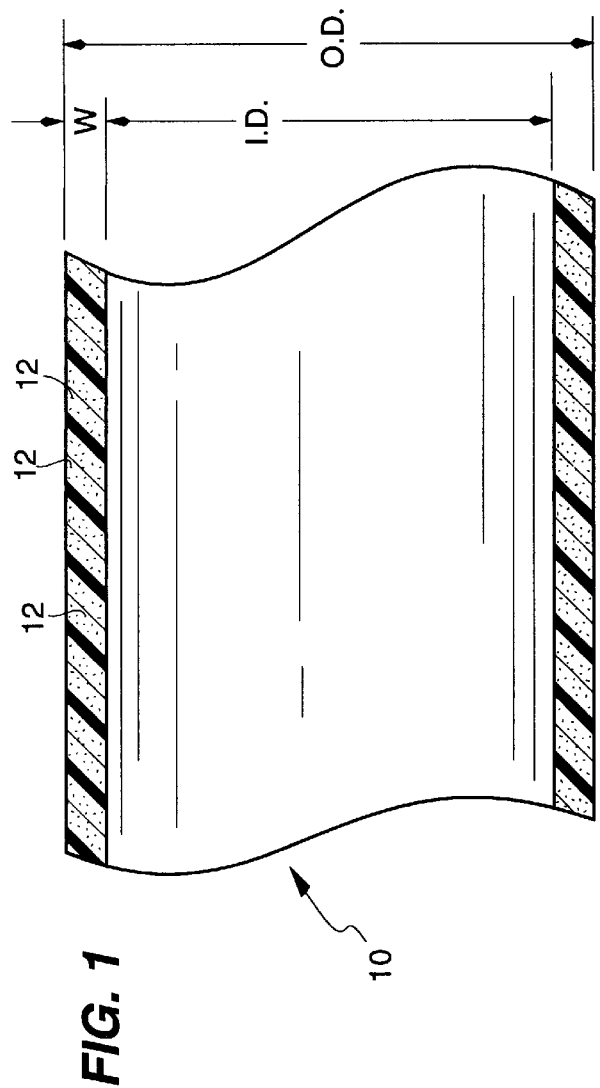
FIG. 1 is a longitudinal sectional view with portions broken away of an extruded tube of plastic material having minute metal particles therein to form a compliant marker band constructed according to the teachings of the present invention.

Referring now to FIG. 1, there is illustrated therein an enlarged cross-section of an extruded tube 10 of plastic material having thoroughly mixed therein minute particles 12 of metal. Metal particles that can be considered for use as the minute particles include platinum, stainless steel, tantalum, and tungsten particles. Presently, tungsten is preferred for its low cost, high radiopaqueness and its availability in particles as small as 0.9 microns.

Figure 3:
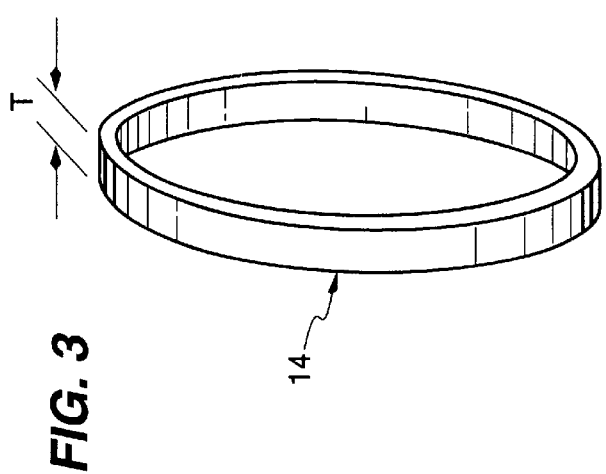
FIG. 3 is a thin marker band sliced, such as with a razor blade, from the extruded tube shown in FIG. 1 or in FIG. 2.

Preferably, the plastic material is one that has heat shrink characteristics so that when a marker band 14 (FIG. 3) is cut from the plastics tube 10, it can be heat shrunk over a catheter or a sheath of a guidewire, thereby eliminating the need for heat or adhesive bonding.

One preferred heat shrinkable material is polyolefin. Other plastic materials that can be used to provide a more compliant or flexible radiopaque extruded tube 10 are polyurethane, PET, or PVC.

Polyurethane is one preferred material since it is relatively flexible such that a whole catheter could be made of a polyurethane tube having minute tungsten particles imbedded therein in sufficient quantity to render the catheter radiopaque.

The tube 10 of compliant marker band material comprises between 10 and 80 percent by weight metal particles and between 90 and 20 percent by weight plastic material.

Figure 2:
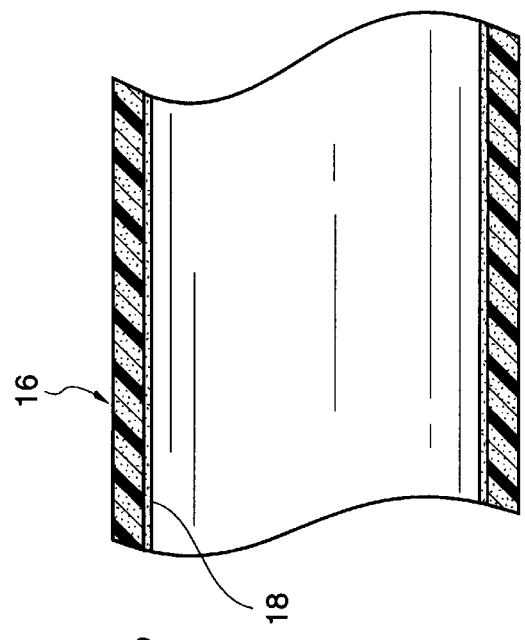
FIG. 2 is a longitudinal sectional view with portions broken away of an extruded tube of plastic material having minute metal particles therein and a having a thin layer of adhesive material on an inner wall surface thereof to form a compliant marker band constructed according to the teachings of the present invention.

In FIG. 2 there is illustrated a modified extruded tube 16 which has on an inner wall surface thereof a thin layer 18 of adhesive, such as by extrusion, whereby both a friction heat shrink and adhesive bond of the band 14 can be established between the band 14 and a catheter or a guidewire sheath over which it is placed.

In addition to the use of thin slices, as small as 0.5 mm of the extruded tube 10 or 16 as marker bands, a length of the tube 10 or 16 of approximately 2 cm. can be utilized as a balloon for a balloon catheter and fused or butt-welded to a polyurethane tubular body of a catheter not having metal particles therein so that only the balloon is radiopaque to enable a doctor to see the balloon on fluoroscopic images or x-ray images.

The heat shrinkable plastic material preferably has a shrinkage of 10 to 20 percent.

It is desirable that the wall thickness W (FIG. 1) of the tube 10 or 16 be between 0.001 inches and 0.020 inches. One preferred wall thickness W is 0.003 inches.

One preferred size of the tube 10 or 16 is a tube having an outer diameter O.D. of approximately 0.039 inches and an inner diameter I.D. of approximately of 0.033 inches.

One preferred thickness T of the marker band 14 is 0.5 mm.

As for the metal particles, the smaller the size the better and preferably not higher than 2 microns. Tantalum particles are currently available at a size of 5 microns.

From the foregoing description, it will be apparent that the tube of compliant radiopaque marker band material 10 or 16 and a band 14 made therefrom of the present invention have a number of advantages, some of which have been described above and others of which are inherent in the invention.

For example, the heat shrinkable nature of the band 14 eliminates the need for bonding the band to a catheter or sheath of a guidewire. Secondly, the extruded tube 10 or 16 can be cut to any desired length, thus enabling the complaint marker band to be custom built to balloon length or any other desirable length since the material is flexible. Finally, by being made of plastic, the compliant marker band 14 or the tubes 10 and 16 do not present a metal surface which can have burrs or other imperfections that could cause trauma to the wall of a blood vessel.

Also it will be understood that modifications can be made to the tubes 10 or 16 and to the compliant marker band 14 of the present invention described above without departing from the teachings of the present invention. Accordingly, the scope of the invention is only to be limited as necessitated by the accompanying claims.

I claim:

1. A tubular medical catheter body comprising a catheter consisting essentially of plastic material having a tubular, flexible, pliable and compliant marker band affixed to and surrounding the external surface of the catheter body, wherein the marker band has an axial length of at least 0.5 mm and not more than 1 cm, which is made from a tubular extrusion of a heat shrinkable plastic material having radiopaque tungsten metal particles therein which are no greater than 2 microns in size and which are thoroughly mixed in said heat shrinkable plastic material, such that said flexible, pliable and compliant marker band is radiopaque throughout.

2. The medical catheter of claim 1, wherein said metal particles are tungsten particles approximately 0.9 microns in size.

3. The medical catheter of claim 1, wherein said compliant marker band has a wall thickness of between 0.001 and 0.020 inches.

4. The medical catheter of claim 3, wherein said compliant marker band has a wall thickness of approximately 0.003 inches.

5. The medical catheter of claim 3, said compliant marker band having being cut from a tube of extruded plastic with said metal particles mixed therein, said tube having an outer diameter of approximately 0.039 inches and an inner diameter of approximately 0.033 inches.

6. The medical catheter of claim 1 wherein said heat shrinkable plastic material has a 10 to 20 percent shrinkability.

7. The medical catheter of claim 1 wherein said heat shrinkable plastic material is polyolefin.

8. The medical catheter of claim 1 wherein said heat shrinkable plastic material is polyurethane.

9. The medical catheter of claim 1, said compliant marker band comprising between 10 and 80 percent by weight metal particles and between 90 and 20 percent by weight plastic.

10. The medical catheter of claim 1, said compliant marker band having a layer of adhesive on an inner wall surface thereof.

* * * * *